US008097103B2

(12) United States Patent
Taylor et al.

(10) Patent No.: US 8,097,103 B2
(45) Date of Patent: Jan. 17, 2012

(54) COPPER COMPLEXES WITH OXALYLDIHYDRAZIDE MOIETIES

(75) Inventors: Robert D. Taylor, Hyrum, UT (US); Gregg Hess, River Heights, UT (US)

(73) Assignee: AUTOLIV ASP, Inc., Ogden, UT (US)

( * ) Notice: Subject to any disclaimer, the term of this patent is extended or adjusted under 35 U.S.C. 154(b) by 169 days.

(21) Appl. No.: 12/486,943

(22) Filed: Jun. 18, 2009

(65) Prior Publication Data
US 2010/0319823 A1    Dec. 23, 2010

(51) Int. Cl.
C06B 41/00 (2006.01)
C06B 31/02 (2006.01)
C06B 29/02 (2006.01)
D03D 23/00 (2006.01)
D03D 43/00 (2006.01)

(52) U.S. Cl. ........... 149/23; 149/61; 149/77; 149/109.2; 149/109.4

(58) Field of Classification Search ............... 149/23, 149/61, 77, 109.2, 109.4
See application file for complete search history.

(56) References Cited

U.S. PATENT DOCUMENTS

| | | | | |
|---|---|---|---|---|
| 3,960,946 A * | 6/1976 | Dewitt et al. | | 564/135 |
| 5,531,941 A * | 7/1996 | Poole | | 264/3.4 |
| 5,889,161 A * | 3/1999 | Bottaro et al. | | 534/551 |
| 5,962,808 A * | 10/1999 | Lundstrom | | 149/19.1 |
| 6,077,371 A | 6/2000 | Lundstrom et al. | | |
| 6,156,136 A | 12/2000 | Bottaro et al. | | |
| 6,562,161 B1 * | 5/2003 | Yamato et al. | | 149/45 |
| 6,651,565 B1 | 11/2003 | Yamato et al. | | |
| 6,689,236 B1 | 2/2004 | Taylor et al. | | |
| 7,040,657 B2 | 5/2006 | Iwai et al. | | |
| 2003/0001369 A1 * | 1/2003 | Iwai et al. | | 280/741 |
| 2007/0246923 A1 * | 10/2007 | Anacker et al. | | 280/741 |

FOREIGN PATENT DOCUMENTS
EP       0505024       6/1996

OTHER PUBLICATIONS

Lewis et al. Inorg. Chem., vol. 12, No. 7, 1973, pp. 1682-1685.*

* cited by examiner

*Primary Examiner* — James McDonough
(74) *Attorney, Agent, or Firm* — Sally J. Brown; Harness Dickey

(57) ABSTRACT

Methods of making and resultant compositions thereof, which include copper-oxalyldihydrazide-based complexes, such as pyrotechnic compositions, gas generants, and ignition materials, which are useful, for example, in inflatable restraint systems. Synthesis of one or more copper-oxalyldihydrazide complexes with nitrate and/or hydroxide counter ions provides a composition that may auto-ignite at a low enough temperature to be based with thermally sensitive gas generants. The present copper-oxalyldihydrazide complexes may also be used in conjunction with various oxidizers to produce compositions with sufficient energy to auto-ignite practically any known pyrotechnic composition.

30 Claims, 1 Drawing Sheet

COPPER COMPLEXES WITH OXALYLDIHYDRAZIDE MOIETIES

FIELD

The present disclosure generally relates to ignitable pyrotechnic compositions, such as gas generant and igniter materials used in inflatable restraint systems, and more particularly to such compositions including copper complexes with oxalyldihydrazide moieties.

INTRODUCTION

The statements in this section provide background information related to the present disclosure and may not constitute prior art.

Passive inflatable restraint systems are used in a variety of applications, such as motor vehicles. Certain types of passive inflatable restraint systems minimize occupant injuries by using a pyrotechnic gas generant to inflate an airbag cushion (e.g., gas initiators and/or inflators) or to actuate a seatbelt tensioner (e.g., micro gas generators), for example. Automotive airbag inflator safety requirements and performance needs continually increase in order to further enhance passenger safety.

Selection and design of compositions and components of gas generant and initiator materials involve addressing various factors, including meeting current industry performance specifications, guidelines, and standards, and generating safe gases or effluents. Handling safety of the gas generant materials, including durational stability, storage, and disposal are also important considerations. With respect to handling and health safety, for example, it may be preferred that the pyrotechnic material compositions are azide-free. Cost of the materials used in selection and design of gas generant and initiator materials is another important consideration.

As such, there is a need for compositions and components that can improve one or more of combustion performance, ignitability, burn rate, auto-ignition temperature, and material costs.

SUMMARY

The present disclosure provides methods and compositions comprising a complex of copper and an oxalyldihydrazide moiety. In various aspects, such a composition comprises a copper-oxalyldihydrazide complex selected from the group consisting of: $Cu(A)_x(NO_3)_2$, $Cu(A)_y(NO_3)(OH)$, and combinations thereof; wherein x is about 1 to about 3, y is about 1 to about 3, and A is an oxalyldihydrazide moiety represented by a general structure of:

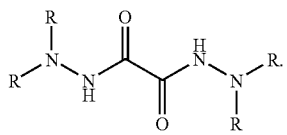

Each R is independently selected from hydrogen, an alkyl group having 1 to 9 carbon atoms, or an aryl group having 1 to 9 carbon atoms. In certain aspects, where each R is respectively selected to be hydrogen, the oxalyldihydrazide moiety A is oxalyldihydrazide (ODH). Pyrotechnic compositions according to the present teachings may further include one or more oxidizers, fuel components, binders, slag promoting agents, and pressing agents, and the like.

In certain aspects of the present teachings, a copper-oxalyldihydrazide complex is provided that comprises $Cu(ODH)_x(NO_3)_2$, where x is about 1 to about 2, and the ODH is oxalyldihydrazide, which is represented by a general structure of:

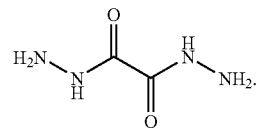

As noted above, each R group in the ODH is selected to be hydrogen.

In yet other variations, a pyrotechnic composition includes a copper-oxalyldihydrazide complex comprising $Cu(ODH)_y(NO_3)(OH)$, where y is about 1 to about 2, optionally about 1.5 to about 2, and optionally about 1.8 to about 1.9. The ODH is oxalyldihydrazide represented by a general structure of:

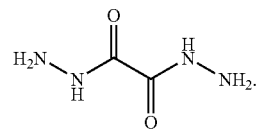

Such pyrotechnic compositions may also include an oxidizer. Suitable oxidizers include alkali and alkaline earth metal nitrates, chlorates, perchlorates, and metal oxides. For example, particularly suitable non-limiting examples of oxidizers include potassium perchlorate, potassium nitrate, sodium nitrate, basic copper nitrate, strontium nitrate, copper oxide, iron oxide, bismuth oxide, and combinations thereof.

BRIEF DESCRIPTION OF THE DRAWING

The present disclosure will become more fully understood from the detailed description and the accompanying drawing, wherein.

DETAILED DESCRIPTION

Figure 1:
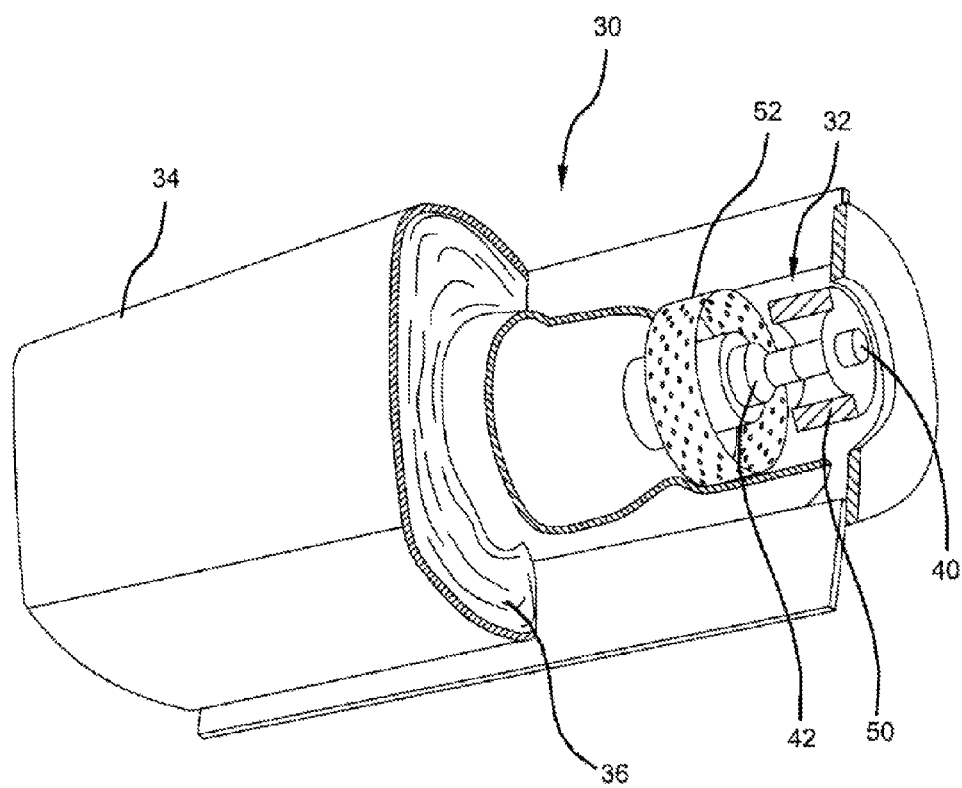
FIG. 1 is a partial cross-sectional view of an exemplary passenger-side airbag module including an inflator for an inflatable airbag restraint device.

Further areas of applicability will become apparent from the description provided herein. It should be understood that the description and specific examples are intended for purposes of illustration only and are not intended to limit the scope of the present disclosure. The citation of references herein does not constitute an admission that those references are prior art or have any relevance to the patentability of the technology disclosed herein. All references cited in the "Detailed Description" section of this specification are hereby incorporated by reference in their entirety.

"A" and "an" as used herein indicate "at least one" of the items is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present disclosure is drawn to improved compositions and methods for making compositions, which can be pyrotechnic compositions used as gas generant and/or ignition materials, by way of non-limiting example. As used herein, the term "composition" refers broadly to a substance containing at least the preferred chemical compound complex or phases, but which may also comprise additional substances or compounds, including impurities. The term "material" also broadly refers to matter containing the preferred compound, complex, or phases. The inventive compositions can be used alone or can be used in combination with other pyrotechnic compositions to form various pyrotechnic materials, like auto-ignition compositions for squibs or igniter cans, or included in gas generant compositions.

The inventive compositions may be used as part of inflatable restraint devices and systems, such as airbag module assemblies, side impact inflators, seatbelt tensioners, hybrid inflators, and other similar applications. Inflatable restraint devices and systems have multiple applications within automotive vehicles, such as driver-side, passenger-side, side-impact, curtain, and carpet airbag assemblies. Other types of vehicles including, for example, boats, airplanes, and trains may also use inflatable restraints. In addition, other types of safety or protective devices may also employ various forms of inflatable restraint devices and systems. Inflatable restraint devices typically involve a series of reactions that facilitate production of gas in order to deploy an airbag or actuate a piston. In the case of airbags, for example, actuation of the airbag assembly system and ignition of the gas generant may inflate the airbag cushion within a few milliseconds.

With reference to FIG. 1, a typical airbag module 30 includes a passenger compartment inflator assembly 32 and a covered compartment 34 to store an airbag 36. Such devices often use a squib or initiator 40 that includes a first igniter material that is electrically ignited when rapid deceleration and/or collision is sensed. The discharge from the squib 40 usually ignites a second initiator or igniter material 42 that burns rapidly and exothermically, in turn igniting a gas generant material 50. The gas generant material 50 burns to produce the majority of gas products directed to the airbag 36 to provide inflation.

The present copper-oxalyldihydrazide complex may be used as an ingredient in a pyrotechnic composition, also referred herein as an ignition or igniter material, propellant, gas-generating material, and the like. The pyrotechnic composition can be in the form of a solid grain, a pellet, a tablet, or the like. Often, a slag or clinker is formed near the pyrotechnic composition (e.g., gas generant or igniter materials) during burning. The slag/clinker serves to sequester various particulates and other compounds generated during combustion. A filter may be provided between the gas generant and airbag in order to remove particulates entrained in the gas and to reduce temperature of the gases prior to entering the airbag.

In various aspects, pyrotechnic compositions include one or more copper-oxalyldihydrazide-based complexes and may further include one or more oxidizers, fuels, or other known additives, whereupon ignition the composition combusts rapidly to form gaseous reaction products (e.g., $CO_2$, $H_2O$, and $N_2$). Rapid combustion releases heat and gaseous products, which may provide heat and energy to combust adjacent gas generant compositions or materials. In certain aspects, the copper-oxalyldihydrazide-based complexes may be a part of a gas generant material. In various aspects, the copper-oxalyldihydrazide-based complexes facilitate heated inflation gas being produced and directed to an inflatable restraint device or used to actuate a piston, for example.

In various embodiments, the copper-oxalyldihydrazide moiety complexes and improved pyrotechnic compositions comprising these copper-oxalyldihydrazide complexes provide a greater thermal safety margin compared to other auto-ignition materials and make possible the use of less expensive gas generants in airbag inflators, for example. For example, a suitable gas generant may include guanidine nitrate and basic copper nitrate or basic copper carbonate, by way of non-limiting example.

Thus, as discussed above, the copper-oxalyldihydrazide-based complexes may be used as a component in pyrotechnic compositions, which generally can include auto-ignition compositions, ignition materials for use in an igniter can or squib, or as a gas generant compositions. In certain embodiments, the copper-oxalyldihydrazide complex may be the primary or sole combustible or ignitable ingredient in such a pyrotechnic composition. In certain aspects, the pyrotechnic compositions may comprise a redox-couple having at least one fuel component, which may be the copper-oxalyldihydrazide complex; optionally additional fuel components may also be included. Depending on whether the fuel component is fully or self-oxidized, or under-oxidized, the composition may include one or more oxidizing components, where the oxidizing component reacts with the fuel component(s) in order to generate the gas product. In certain aspects, the copper-oxalyldihydrazide-based complexes of the present disclosure are combined with one or more oxidizer components, which may in certain aspects improve stoichiometry of the combustion reaction to reduce potentially detrimental incomplete combustion products.

Synthesis of one or more of the inventive copper-oxalyldihydrazide complexes with nitrate and/or hydroxide counter ions is provided by the methods of the present teachings. In certain aspects, such a complex auto-ignites at a relatively low temperature, so that it can be safely based or combined with thermally sensitive gas generants to ignite such accompanying gas generant compositions. The inventive copper-oxalyldihydrazide complexes may also be used in conjunction with various oxidizers to produce pyrotechnic compositions with sufficient energy to auto-ignite other pyrotechnic compositions. For example, compositions containing the present inventive copper-oxalyldihydrazide-based complexes may be used to auto-ignite gas generant inflators at temperatures of less than or equal to about 185° C., optionally less than or equal to about 170° C., optionally less than or equal to about 165° C., optionally less than or equal to about 155° C., and in some aspects less than or equal to about 150° C., thus providing various advantages in comparison to conventional auto-ignition materials. For example, many conventional auto-ignition materials have auto-ignition temperatures that exceed 185° C., and thus potentially impose limits on design options for various pyrotechnic materials. In certain aspects, the inventive pyrotechnic compositions comprising copper-oxalyldihydrazide-based complexes have an auto-ignition temperature that is less than or equal to about 185° C. and greater than or equal to about 150° C.; optionally less than or equal to about 170° C. and greater than or equal to about 150° C.; optionally less than or equal to about 170° C. and greater than or equal to about 155° C.; and in certain variations, less than or equal to about 170° C. and greater than or equal to about 165° C.

As illustrated in Reactions (1) and (2) below, the present methods and compositions include copper-oxalyldihydrazide-based complexes with nitrate and/or hydroxide counter ions. "Oxalyldihydrazide-based," "oxalyldihydrazide moiety" and "oxalyldihydrazide-derivative" are used interchangeably to refer to a portion of the complex that comprises an oxalyldihydrazide-derived moiety (referred to herein as "A"), represented by a general structure of:

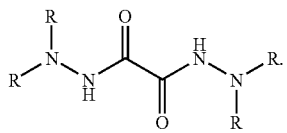

Each R in the an oxalyldihydrazide-derived moiety is independently selected from hydrogen, an alkyl group having 1 to 9 carbon atoms, or an aryl group having 1 to 9 carbon atoms. When each R group is selected to be hydrogen (H), oxalyldihydrazide (ODH) is formed, as represented by a general structure of:

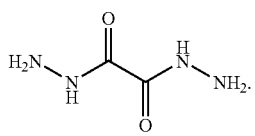

In various aspects, a copper-oxalyldihydrazide-based complex of the present teachings includes copper II complexed with oxalyldihydrazide (chemical formula $C_2H_6N_4O_2$; in other words oxalic acid hydrazide) or an oxalyldihydrazide derivative or moiety. In particular, copper-oxalyldihydrazide-based complexes include those formed by Reactions (1) and (2):

$$Cu(NO_3)_2 + xC_2H_6N_4O_2 \rightarrow Cu(C_2H_6N_4O_2)_x(NO_3)_2 \quad (1)$$

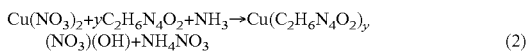

$$Cu(NO_3)_2 + yC_2H_6N_4O_2 + NH_3 \rightarrow Cu(C_2H_6N_4O_2)_y(NO_3)(OH) + NH_4NO_3 \quad (2)$$

where x is about 1 to about 3 and y is about 1 to about 3.

The copper-oxalyldihydrazide-based complexes may include a single species (e.g., oxalyldihydrazide moiety or oxalyldihydrazide derivative moiety, or particular counter ions) and/or may include a single or substantially constant stoichiometric ratio of copper and oxalyldihydrazide-based moiety to nitrate and/or hydroxide. Alternatively, the copper-oxalyldihydrazide-based complex may include a mixture of species and/or a range of stoichiometric ratios. The stoichiometric ratios of copper-oxalyldihydrazide-based moiety to nitrate and/or hydroxide may range from about 1:2 to about 3:2 (copper-oxalyldihydrazide:nitrate) for Reaction (1), where x is about 1 to about 3, and from range from 1:1:1 to 3:1:1 (copper-oxalyldihydrazide:nitrate:hydroxide) for Reaction (2), where y is about 1 to about 3. However, in some embodiments, the value of x is about 1.5 to about 2. In certain embodiments, the value of y is about 1 to about 2. In yet other embodiments, the value of y may range from greater than or equal to about 1.5 to less than or equal to about 1.9, optionally from greater than or equal to about 1.8 to less than or equal to about 1.9; and in certain aspects, optionally about 1.86.

As noted above, in various aspects, an oxalyldihydrazide moiety (referred to herein as "A") may include oxalyldihydrazide derivatives, such as various alkyl- and arylhydrazides of oxalic acid. Examples include oxalic acid, bis(2-methyl-hydrazide); oxalic acid, bis(2-ethylhydrazide); oxalic acid, hydrazide 2-isopropylhydrazide; oxalic acid, hydrazide 2-phenethylhydrazide; oxalic acid, bis(2-propylhydrazide), and combinations thereof. For example, as described above, the copper-oxalyldihydrazide-based complex may include A, the oxalyldihydrazide-based moiety represented by the general structure:

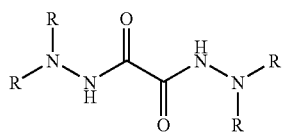

where each R is independently H or an alkyl group or an aryl group, respectively having 1 to 9 carbon atoms. When each R is selected to be H, the compound is oxalyldihydrazide (ODH) having a structure represented by a general structure of:

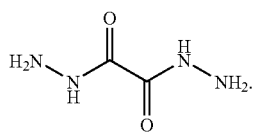

In various aspects, the present copper-oxalyldihydrazide complexes can advantageously impart low-temperature auto-ignition characteristics to pyrotechnic compositions, such as to a gas generant material. For example, the copper-oxalyldihydrazide-based complexes formed by Reactions (1) and (2) are capable of auto-ignition at standard pressure and a temperature of about 150° C. to about 170° C., depending on the particular substituents present in the complex.

In certain aspects, the copper-oxalyldihydrazide-based complex may not be fully oxidized to produce combustion reaction products $CO_2$ and $H_2O$ during the combustion reaction. Hence in certain embodiments, the copper-oxalyldihydrazide-based complex is mixed with an oxidizer composition to alter the combustion reaction stoichiometry to better favor complete combustion to primarily form $CO_2$ and $H_2O$, for example. In certain variations, copper-oxalyldihydrazide-based complexes can be combined with an oxidizer to favor production of non-toxic gas during combustion of the gas generant. For example, the copper-oxalyldihydrazide-based complexes can be used as an auto-ignition composition, which is combined with an oxidizer and optionally with other conventional ingredients, such as fuels to form pyrotechnic compositions.

Suitable oxidizers include, by way of non-limiting example: alkali, alkaline earth, and ammonium nitrates; nitrites; chlorates and perchlorates; metal oxides; basic metal nitrates; transition metal complexes of ammonium nitrate; iodates; permanganates; metal oxides; metal hydroxy nitrates; and combinations thereof. The oxidizer may be selected, along with the copper-oxalyldihydrazide complex and/or additional fuel component(s), to form a gas generant that upon combustion achieves an effectively high burn rate and gas yield from the fuel. Specific examples of suitable oxidizers include basic metal nitrates such as basic copper nitrate. Basic copper nitrate has a high oxygen-to-metal ratio and good slag forming capabilities upon burn. Such oxidizing agents may be present in any amount; however in certain aspects, an oxidizer is present in an amount of less than or equal to about 50% by weight of the total pyrotechnic composition; optionally less than or equal to about 40%; optionally less than or equal to about 30%; optionally less than or equal to about 25%; optionally less than or equal to about 20%; optionally less than or equal to about 15%; optionally less than or equal to about 10%; and optionally greater than 0 and less than or equal to about 5% of the total pyrotechnic composition. In certain aspects, the amount of oxidizer is present at about 10% to about 50% by weight of the total pyrotechnic composition.

Additional examples of suitable oxidizers include water soluble oxidizing compounds, such as for example, ammonium nitrate, sodium nitrate, strontium nitrate, potassium nitrate, ammonium perchlorate, sodium perchlorate, and potassium perchlorate. Also included are ammonium dinitramide and perchlorate-free oxidizing agents. The composition may include combinations of oxidizers, such that the various oxidizers may be nominally considered as including a primary oxidizer, a second oxidizer, and the like. For example, at least one copper-oxalyldihydrazide complex and optionally an additional fuel component, such as guanidine nitrate, may be mixed with a combination of oxidizers, such as basic copper nitrate and potassium perchlorate, to form a gas generant.

In certain aspects, the pyrotechnic compositions include both the copper-oxalyldihydrazide-based complex, and may also include one or more additional fuel components. Such fuels include: boron, zirconium, titanium hydride, silicon, guanidine derivatives, tetrazoles, bitetrazoles, guanylurea derivatives, copper complexes and guanylurea derivatives, cyclotrimethylenetrinitramine (RDX), octahydro-1,3,5,7-tetranitro-1,3,5,7-tetrazocane (HMX), and other nitrogen-containing compounds. Additional examples of fuel components include: tetrazole salts, such as aminotetrazole and mineral salts of tetrazole; 1,2,4-triazole-5-one and 3-nitro-1,2,4-triazole-5-one; guanidine nitrate; nitro guanidine; amino guanidine nitrate; metal nitrates; and the like. These fuels may be categorized as gas generant fuels due to their relatively low burn rates and are often combined with one or more oxidizers in order to achieve desired burn rates and gas production.

In some embodiments, the fuel component may be a non-azide nitrogen-containing fuel compound, such as an organic fuel, including one or more of guanidine nitrate, nitroguanidine, aminoguanidine nitrate, diaminoguanidine nitrate, triaminoguanidine nitrate, guanylurea nitrate, tetrazoles, bitetrazaoles, azodicarbonamide and mixtures thereof. Particular non-azide nitrogen-containing fuel compounds include guanidine nitrate and hexamine cobalt III nitrate. Use of guanidine nitrate in gas generant compositions is generally based on a combination of factors relating to cost, thermal stability, availability, and compatibility with other composition components.

Compositions of the present copper-oxalyldihydrazide complex may further include one or more additives, such as binders, coolants, and slag forming agents. The binder component may comprise cellulosic derivatives, thermosetting binders, or thermoplastic binders. For example, a polymeric binder material can be used to impart sufficient cohesive properties to the composition to make the composition extrudable. Extrudable compositions in accordance with certain embodiments may include or contain about 1 to about 20 weight percent of such a polymeric binder component. Suitable binder matrices and associated non-energetic binders, plasticizers, and stabilizers, include those as disclosed in U.S. Pat. No. 6,689,236 to Taylor et al., the relevant portions of which are incorporated by reference.

In some instances, one or more of the materials or components included in the present compositions may serve more than one role or function. For example, binder materials may also act or function as a fuel component, as described herein. Thus, specific range limits for particular materials that may be included in the present compositions are generally dependent, at least in part, on what other particular materials are included. Range limits for particular materials can be identified by those skilled in the art and guided by the teachings provided herein.

Further examples of binder materials include cellulose and cellulose-derivative binders, or cellulosics, such as ethyl cellulose, carboxymethyl cellulose, hydroxypropyl cellulose and combinations of two or more thereof. Other suitable binders include natural gums, polyacrylates, polyacrylamides, polyurethanes, polybutadienes, polystyrenes, polyvinyl alcohols, polyvinyl acetate, silicones and combinations of two or more thereof. Suitable natural gum binder materials may include guar, xanthan, Arabic gum and combinations of two or more thereof. Incorporation of binder materials, such as the above-described cellulosic binders, may result in or form compositions that burn at lower temperatures. These "cooler burning" materials may be preferable for certain applications.

Pyrotechnic compositions, like gas generants compositions, prepared via extrusion processing may also exhibit increased or maximized loading densities and therefore serve to reduce or minimize the required chamber volume associated therewith. Such extruded compositions may burn more easily at higher pressure conditions and can reduce or minimize the production or yield of incomplete combustion products having the general form of $CO_x$ and $NO_x$, for example.

The composition may include a coolant in order to reduce the burning rate of the pyrotechnic (e.g., gas generant) composition, for example. In practice, the composition may include a coolant in the range of up to about 20 weight percent. Suitable coolants include, but are not limited to, oxalic acid, ammonium oxalate, oxamide, ammonium carbonate, calcium carbonate, magnesium carbonate, and combinations thereof.

Additional additives such as slag forming agents, flow aids, plasticizers, viscosity modifiers, pressing aids, dispersing aids, or phlegmatizing agents may also be included in the composition in order to facilitate processing or to provide enhanced properties. For example, compositions in accordance with the invention may include a slag forming agent such as a metal oxide; e.g., aluminum oxide. Generally, such additives may be included in the present compositions in an amount of about 1 to about 5 weight percent of the total composition. Slag and viscosity modifying/promoting agents include cerium oxide, ferric oxide, zinc oxide, aluminum oxide, titanium oxide, zirconium oxide, bismuth oxide, molybdenum oxide, lanthanum oxide, silicon dioxide, combinations thereof, and the like. Such redox inert oxides may be employed individually or as mixtures of two or more individual components. For example, where one oxide has a very fine form (e.g., particle size of less than about 20 nm) useful for improving viscosity of the mixture slurry, another coarser oxide having larger particle sizes may be provided to the mixture to improve slagging properties without interfering with or negatively affecting burning rate.

Pressing aids may also be added to the composition prior to tableting or pressing and include compounds such as calcium or magnesium stearate, graphite, molybdenum disulfide, tungsten disulfide, boron nitride, and mixtures thereof at conventional levels known to those of skill in the art. For example, the pressing aid(s) may be included at about 1 to about 3 weight percent.

In some embodiments, the present copper-oxalyldihydrazide complexes and compositions incorporating such complexes may be used or combined with other known pyrotechnic compositions for the purposes of imparting auto-ignition characteristics. For instance, including one or more of the copper-oxalyldihydrazide complexes in a mixture of boron/potassium nitrate can result in an igniter material that auto-ignites at low temperatures, such as a temperature of about 150° C. to about 170° C. The copper-oxalyldihydrazide complexes may also be incorporated in squibs, microgas generators, as well as airbag inflators where the devices could potentially explode if heated to a relatively high temperature. The relatively low auto-ignition compositions would consequently provide ignition at a lower temperature, where the devices would function normally without potentially rupturing the device.

Five representative auto-ignition compositions that include the present copper-oxalyldihydrazide complexes are shown in Table 1:

TABLE 1

| Ingredient | Ex. 1 | Ex. 2 | Ex. 3 | Ex. 4 | Ex. 5 |
|---|---|---|---|---|---|
| $Cu(ODH)1.5(NO_3)_2$ | 75.36 | — | 72.38 | — | 20 |
| $Cu(ODH)1.86(NO_3)(OH)$ | — | 61.56 | — | 57.86 | — |
| Potassium perchlorate | 24.64 | 38.44 | — | — | 32.60 |
| Potassium Nitrate | — | — | 27.62 | 42.14 | — |
| Guanidine Nitrate | — | — | — | — | 47.40 |
| Autoignition temp (° C.) | 163 | 168 | 163 | 168 | 163 |

*Note:
Compositions are given in weight percent; auto-ignition temperature is the temperature at which the materials will openly burn at a temperature ramp rate of 10° C./minute; ODH = oxalyldihydrazide ($C_2H_6N_4O_2$).

Representative Compositions Ex. 1, 3, and 5 are examples of the product of Reaction (1), where x is about 1.5. Representative Compositions Ex. 2 and 4 are examples of the product of Reaction (2), where y is about 1.86.

In certain aspects, the composition may include about 50-80 parts by weight of the copper-oxalyldihydrazide complex and optionally one or more additional fuels (e.g., guanidine nitrate), about 20-60 parts by weight of oxidizers (e.g., potassium perchlorate), and about 0-5 parts by weight of additives, such as slag forming agents like silica ($SiO_2$) or equivalents thereof.

Methods for making copper-oxalyldihydrazide complexes include mixing components of Reactions (1) and/or (2) above at room temperature in water. As per Reaction (1), an aqueous mixture of copper nitrate and oxalyldihydrazide may be used to form the copper-oxalyldihydrazide complex of $Cu(C_2H_6N_4O_2)_x(NO_3)_2$, where x is about 1 to about 3. As per Reaction (2), an aqueous mixture of copper nitrate, oxalyldihydrazide, and ammonia may be used to form the copper-oxalyldihydrazide complex of $Cu(C_2H_6N_4O_2)_y(NO_3)(OH)$, where y is about 1 to about 3.

For example, Representative Composition 3 in Table 1, which forms the product of Reaction (1), may be prepared as follows. 468.3 grams of oxalyldihydrazide and 1,000 grams of distilled water are stirred together to dissolve as much of the oxalyldihydrazide as possible at room temperature. To this mixture, 461.7 grams of hydrated copper(II) nitrate, $Cu(NO_3)_2 \cdot 2.5H_2O$ is added, as a solid material. This mixture is stirred for a period of about one hour. During this one hour, a blue complex is formed as a precipitate in the mixture indicative of reaction. The precipitate is collected by vacuum filtration and washed with 500 grams of distilled water and collected by re-filtering the washed mixture. To the wet complex cake, 276.2 grams of $KNO_3$ is added. This slurry mixture is machine-mixed in a Hobart mixer for about 30 minutes without the addition of any extra water. Following slurry mixing, the material is dried in a stainless steel pan at 60° C. for approximately 5 hours. The dried material is then co-milled to form a course powder and tableted using a rotary tablet machine to form about 0.125 inch (0.317 cm) diameter by about 0.09 inch (0.229 cm) thick cylindrical tablets. Such tablets may be blended with other compositions or tablets, such as gas generant tablets, and loaded in airbag inflators.

Thus, the present copper-oxalyldihydrazide complexes and auto-ignition materials including these complexes may be used in conjunction with one or more gas generants that contain components such as guanidine nitrate, basic copper nitrate, potassium perchlorate, and other metal oxide additives.

Other methods including making compositions, such as gas generant compositions, that include one or more of the present copper-oxalyldihydrazide complexes. For example, in various embodiments a gas generant composition may be formed by combining dry or relatively dry components that include at least one fuel component that includes one or more of the present copper-oxalyldihydrazide complexes, a binder matrix component, a stabilizer component, and any additional components, such as oxidizers, coolants, slag promoters, and the like. These materials may be dry blended and extruded and/or tableted.

In some embodiments, a method of making a composition includes mixing the various components with a solvent in order to form a viscous paste. The paste may then be extruded and cut to form cylindrical pellets, grains or extrudlets. The use of a plasticizer, for example such as dimethyl malonate, may reduce the amount of solvent required for extrusion and minimize the dimensional changes which occur during the drying of the wet extrudlets. Solvents suitable for use in the preparation of such gas generant extrudlets include alcohols, ketones, ethyl acetate, butyl acetate, and combinations thereof. The dried composition particles or powder may be readily pressed into pellets, grains, tablets, cylinders, or other geometries to produce a material suitable for use as a gas-generating charge in inflatable restraints; e.g., a vehicle airbag.

The pressing operation may be facilitated by mixing the components with a quantity of water or other pressing aid, such as graphite powder, calcium stearate, magnesium stearate, and/or graphitic boron nitride, by way of non-limiting example. The water may be provided in the form of a mixture of water and hydrophobic fumed silica, which may be mixed with the particles using a high shear mixer. The composition may then be pressed into various forms, such as pellets or grains.

In some embodiments, the compositions are formed into pellets or grains having densities from about 1.8 g/cm³ to about 2.2 g/cm³. These pellets and granular forms may be readily ignited by an igniter, such as an electric squib, or in certain aspects, by an igniferous booster comprising pyrotechnic sheet material. The pyrotechnic sheet material may be formed of an oxidizing film, for example, a film of polytetrafluoroethylene coated with a layer of oxidizable metal, such as magnesium, as described in European Patent Publication No. 0505024 to Graham et al., the relevant portions of which are incorporated by reference.

In certain embodiments, a composition, such as a gas-generant composition, may be formed from an aqueous dispersion of the copper-oxalyldihydrazide complex and optionally an additional fuel component that are added to an aqueous solution where one or more oxidizer components are dispersed and stabilized, either dissolved in the solution themselves, or provided as a stable dispersion of solid particles. The solution or dispersion may also be in the form of a slurry.

The mixture of components forming the aqueous dispersion may also take the form of a slurry that is a flowable or pumpable mixture of fine (relatively small particle size) and substantially insoluble particle solids suspended in a liquid vehicle or carrier. Mixtures of solid materials suspended in a carrier are also contemplated. In some embodiments, the slurry comprises particles having an average maximum particle size of less than about 500 μm, optionally less than or equal to about 200 μm, and in some cases, less than or equal to about 100 μm.

The slurry contains flowable and/or pumpable suspended solids and other materials in a carrier. Suitable carriers include aqueous solutions that may be mostly water; however, the carrier may also contain one or more organic solvents or alcohols. In some embodiments, the carrier may include an azeotrope, which refers to a mixture of two or more liquids, such as water and certain alcohols that desirably evaporate in constant stoichiometric proportion at specific temperatures and pressures. The carrier should be selected for compatibility with the fuel and oxidizer components to avoid adverse reactions and further to maximize dispersability and/or solubility of the several components forming the slurry. Non-limiting examples of suitable carriers include water, isopropyl alcohol, n-propyl alcohol, and combinations thereof.

In certain embodiments, the slurry has a water and/or solvent content of greater than or equal to about 15% by weight and may be greater than or equal to about 20%, 30%, or 40% by weight of the total slurry. In some embodiments, the water and/or solvent content is about 15% to 85% by weight of the total slurry weight. As the water and/or solvent content increases, the viscosity of the slurry decreases, thus pumping and handling become easier. In some embodiments, the slurry has a viscosity ranging from about 50,000 to 250,000 centipoise. Such viscosities can provide suitable rheological properties that allow the slurry to flow under applied pressure, but also permit the slurry to remain stable.

The oxidizer components may be uniformly dispersed in the fuel solution by vigorous agitation to form the dispersion, where the particles of oxidizer are separated to a sufficient degree to form a stable dispersion. In the case of water insoluble oxidizers, the viscosity will reach a minimum upon achieving a fully or near fully dispersed state. A high shear mixer may be used to achieve efficient dispersion of the oxidizer particles. The viscosity of the dispersion should be sufficiently high to prevent any substantial migration (i.e., fall-out or settling) of the solid particles in the mixture.

In some embodiments, a quantity of silica ($SiO_2$) is included in the aqueous dispersion, which can act as a slag-modifying compound but also serves to thicken the dispersion and reduce or prevent migration of solid oxidizer particles in the bulk dispersion. The silica can also react with the oxidizer during ignition to form a glassy slag that is easily filtered out of the gas produced upon ignition of the gas generant. The silica is preferably in very fine form, for example, and may have particle sizes of about 7 nm to about 20 nm, although in certain aspects, silica having particles sizes of up to about 50 μm may be employed as well.

The present methods and compositions provide copper-oxalyldihydrazide complexes that may be used to improve gas generants and other combustible materials. In particular, the present compositions and methods make possible a gas generant without resorting to expensive ingredients, such as tetrazoles, bitetrazoles, and the like, all the while employing traditional fabrication and process methods. In addition, gas generants including the copper-oxalyldihydrazide complex provides low toxicity and high gas outputs, and are desirably thermally stable; i.e., decompose only at temperatures greater than about 185°; optionally greater than about 175° C.; optionally greater than about 170° C.; optionally greater than about 165° C.; optionally greater than about 160° C.; optionally greater than about 155° C.

In addition, the present compositions overcome a common shortcoming of various non-azide gas generant formulations that often exhibit a tendency to be difficult to ignite. Inflator devices used in automotive inflatable restraint systems commonly include or incorporate relatively intricate and oftentimes expensive ignition systems, such as in the form of an ignition train, to provide or result in desired ignition and proper functioning of the gas generant formulation. Consequently, the present inventive compositions provide a means to reduce or eliminate or reduce the size of the ignition train, potentially saving significant costs for automotive inflatable restraint systems.

The examples and other embodiments described above are not intended to be limiting in describing the full scope of compositions and methods of this technology. Equivalent changes, modifications and variations of specific embodiments, materials, compositions, and methods may be made within the scope of the present disclosure with substantially similar results.

What is claimed is:

1. A composition comprising a copper-oxalyldihydrazide complex selected from the group consisting of: $Cu(A)_x(NO_3)_2$, $Cu(A)_y(NO_3)(OH)$, and combinations thereof; wherein x is about 1 to about 3, y is about 1 to about 3, and A is an oxalyldihydrazide-based moiety represented by a general structure of:

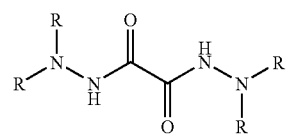

wherein each R is independently selected from hydrogen, an alkyl group having 1 to 9 carbon atoms, or an aryl group having 1 to 9 carbon atoms, wherein the copper-oxalyldihydrazide complex is present at about 50 to about 80 weight percent of a total amount of the composition.

2. The composition of claim 1, wherein the copper-oxalyldihydrazide complex comprises $Cu(A)_x(NO_3)_2$ and $Cu(A)_y(NO_3)(OH)$.

3. The composition of claim 1, wherein the oxalyldihydrazide-based moiety A is selected from the group consisting of: oxalic acid, bis(2-methylhydrazide); oxalic acid, bis(2-ethylhydrazide); oxalic acid, hydrazide 2-isopropylhydrazide; oxalic acid, hydrazide 2-phenethylhydrazide; oxalic acid, bis(2-propylhydrazide); and combinations thereof.

4. The composition of claim 1, further comprising an oxidizer.

5. The composition of claim 4, wherein the oxidizer comprises a member selected from the group consisting of: alkali, alkaline earth, and ammonium nitrates and nitrites; chlorates and perchlorates; metal oxides; basic metal nitrates; transition metal complexes of ammonium nitrate; iodates; permanganates; metal oxides; metal hydroxy nitrates; and combinations thereof.

6. The composition of claim 4, wherein the oxidizer comprises a member selected from the group consisting of: potassium perchlorate, potassium nitrate, and combinations thereof.

7. The composition of claim 4 comprising the oxidizer at about 20 to about 50 weight percent of a total amount of the composition.

8. The composition of claim 1, further comprising a fuel component.

9. The composition of claim 8, wherein the fuel component comprises a member selected from the group consisting of: boron, zirconium, titanium hydride, silicon, guanidine derivatives, tetrazoles, bitetrazoles, guanylurea derivatives, copper complexes and guanylurea derivatives, cyclotrimethylenetrinitramine (RDX), octahydro-1,3,5,7-tetranitro-1,3,5, 7-tetrazocane (HMX), tetrazole salts, aminotetrazole and mineral salts of tetrazole; 1,2,4-triazole-5-one; 3-nitro-1,2,4-triazole-5-one; guanidine nitrate; nitro guanidine; amino guanidine nitrate; metal nitrates; diaminoguanidine nitrate, triaminoguanidine nitrate, guanylurea nitrate, azodicarbonamide, hexamine cobalt III nitrate, and combinations thereof.

10. The composition of claim 8, wherein the fuel component comprises guanidine nitrate.

11. The composition of claim 8 comprising the fuel component and the copper-oxalyldihydrazide complex that combined are present at about 50 to about 80 weight percent of the total amount of the composition.

12. The composition of claim 1, further comprising a binder.

13. The composition of claim 12, wherein the binder comprises a member selected from the group consisting of: cellulose and cellulose-derivative binders, ethyl cellulose, carboxymethyl cellulose, hydroxypropyl cellulose; natural gums, guar, xanthan, Arabic; polyacrylates; polyacrylamides; polyurethanes; polybutadienes; polystyrenes; polyvinyl alcohols; polyvinyl acetates; silicones; and combinations thereof.

14. The composition of claim 1, further comprising a coolant.

15. The composition of claim 14, wherein the coolant comprises a member selected from the group consisting of: oxalic acid, ammonium oxalate, oxamide, ammonium carbonate, calcium carbonate, magnesium carbonate, and combinations thereof.

16. The composition of claim 1, further comprising a slag forming agent.

17. The composition of claim 16, wherein the slag forming agent comprises a member selected from the group consisting of: cerium oxide, ferric oxide, zinc oxide, aluminum oxide, titanium oxide, zirconium oxide, bismuth oxide, molybdenum oxide, lanthanum oxide, and combinations thereof.

18. The composition of claim 1 having an auto-ignition temperature of about 150° C. to about 185° C.

19. A copper-oxalyldihydrazide complex comprising $Cu(ODH)_x(NO_3)_2$, wherein x is about 1 to about 2 and the ODH is oxalyldihydrazide represented by a general structure of:

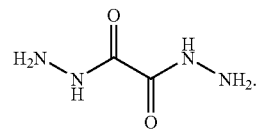

wherein the copper-oxalyldihydrazide complex is present at about 50 to about 80 weight percent of a total amount of the composition.

20. The copper-oxalyldihydrazide complex of claim 19, wherein x is about 1.5.

21. The copper-oxalyldihydrazide complex of claim 19, further comprising an oxidizer selected from the group consisting of: alkali, alkaline earth, and ammonium nitrates and nitrites; chlorates and perchlorates; metal oxides; basic metal nitrates; transition metal complexes of ammonium nitrate; iodates; permanganates; metal oxides; metal hydroxy nitrates; and combinations thereof.

22. The copper-oxalyldihydrazide complex of claim 21, wherein the oxidizer comprises a member selected from the group consisting of: potassium perchlorate, potassium nitrate, and combinations thereof.

23. The copper-oxalyldihydrazide complex of claim 19 having an auto-ignition temperature of about 160 to about 165° C.

24. The copper-oxalyldihydrazide complex of claim 19 having an auto-ignition temperature of about 163° C.

25. A pyrotechnic composition comprising:
a copper-oxalyldihydrazide complex comprising $Cu(ODH)_y(NO_3)(OH)$, wherein y is about 1.86, and the ODH is oxalyldihydrazide represented by a general structure of:

and an oxidizer.

26. The pyrotechnic composition of claim 25, wherein the oxidizer comprises a member selected from the group consisting of: alkali, alkaline earth, and ammonium nitrates and nitrites; chlorates and perchlorates; metal oxides; basic metal nitrates; transition metal complexes of ammonium nitrate; iodates; permanganates; metal oxides; metal hydroxy nitrates; and combinations thereof.

27. The pyrotechnic composition of claim 25, wherein the oxidizer comprises a member selected from the group consisting of: potassium perchlorate, potassium nitrate, and combinations thereof.

28. The pyrotechnic composition of claim 25 having an auto-ignition temperature of about 150° C. to about 170° C.

29. A composition comprising a copper-oxalyldihydrazide complex comprising $Cu(A)_x(NO_3)_2$ and $Cu(A)_y(NO_3)(OH)$; wherein x is about 1 to about 3, y is about 1 to about 3, and A is an oxalyldihydrazide-based moiety represented by a general structure of:

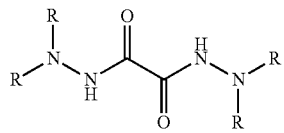

wherein each R is independently selected from hydrogen, an alkyl group having 1 to 9 carbon atoms, or an aryl group having 1 to 9 carbon atoms.

30. A composition comprising a copper-oxalyldihydrazide complex selected from the group consisting of: $Cu(A)_x(NO_3)_2$, $Cu(A)_y(NO_3)(OH)$, and combinations thereof; wherein x is about 1 to about 3, y is about 1 to about 3, and A is an oxalyldihydrazide-based moiety represented by a general structure of:

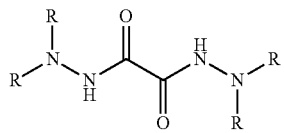

wherein each R is independently selected from hydrogen, an alkyl group having 1 to 9 carbon atoms, or an aryl group having 1 to 9 carbon atoms; and an oxidizer present at about 20 to about 50 weight percent of a total amount of the composition.

* * * * *